United States Patent [19]

Weigert

[11] Patent Number: 4,593,124

[45] Date of Patent: Jun. 3, 1986

[54] PROCESS FOR PREPARING A MIXTURE OF METHYL- OR ETHYL-SUBSTITUTED PRIMARY ANILINES

[75] Inventor: Frank J. Weigert, Wilmington, Del.

[73] Assignee: E. I. Du Pont de Nemours and Company, Wilmington, Del.

[21] Appl. No.: 649,711

[22] Filed: Sep. 12, 1984

Related U.S. Application Data

[63] Continuation-in-part of Ser. No. 559,183, Dec. 7, 1983, abandoned.

[51] Int. Cl.$^4$ .................................................. C07C 85/24
[52] U.S. Cl. ................................................................ 564/409
[58] Field of Search .......................................... 564/409

[56] References Cited

U.S. PATENT DOCUMENTS

| | | | |
|---|---|---|---|
| 3,733,365 | 5/1973 | Yeakey et al. | 564/409 X |
| 3,868,420 | 2/1975 | Evans et al. | 564/409 X |
| 3,931,298 | 1/1975 | Wollensak | 564/409 X |
| 3,960,962 | 6/1976 | Shubkin | 564/409 X |
| 4,188,341 | 2/1980 | Fischer | 564/409 X |
| 4,317,931 | 3/1982 | Wollensak | 564/409 |
| 4,480,128 | 10/1984 | Arpe et al. | 564/409 UX |

FOREIGN PATENT DOCUMENTS

| | | | |
|---|---|---|---|
| 92103 | 4/1982 | European Pat. Off. | 564/409 |
| 29178 | 8/1974 | Japan | 564/409 |
| 28128 | 3/1978 | Japan | 564/409 |
| 28129 | 3/1978 | Japan | 564/409 |

OTHER PUBLICATIONS

Inoue et al., "Seikyu Gakkaishi", 15 p. 372, (1972).
Matsumoto et al., "Chemistry Letters", pp. 435–438, (1978).

*Primary Examiner*—Paul F. Shaver

[57] ABSTRACT

A process is disclosed for preparing an isomeric mixture of a monomethyl-, dimethyl- or monoethyl-substituted aniline consisting essentially of contacting at least one of said anilines with a specified zeolite at about 250°–500° C. and about 10 kPa–10 MPa of pressure.

14 Claims, 1 Drawing Figure

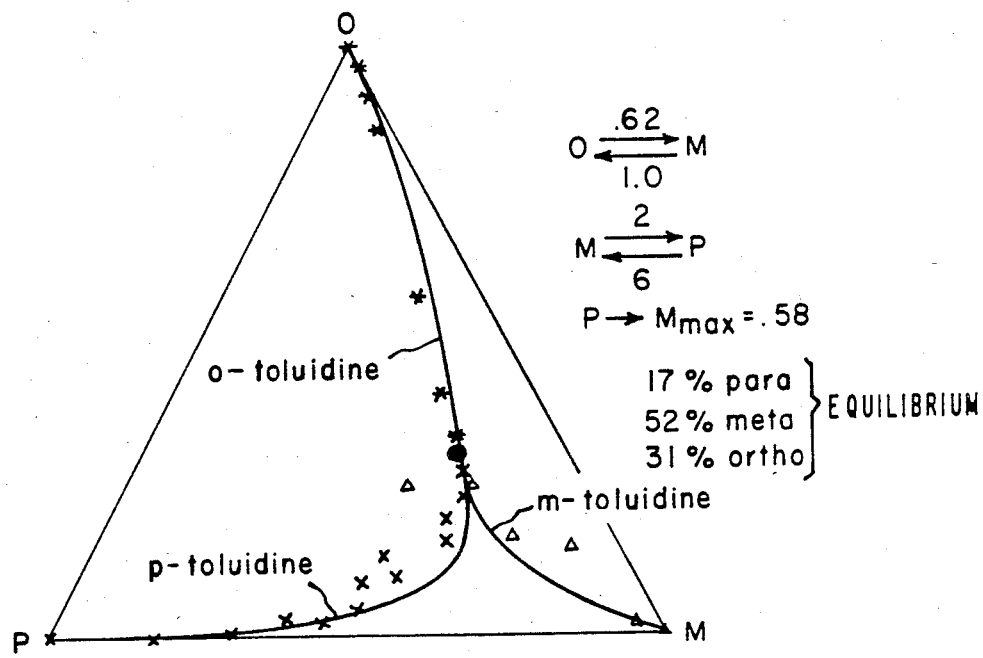

PROCESS FOR PREPARING A MIXTURE OF METHYL- OR ETHYL-SUBSTITUTED PRIMARY ANILINES

CROSS-REFERENCE TO RELATED APPLICATION

This is a continuation-in-part of application bearing U.S. Ser. No. 559,183, filed on Dec. 7, 1983, now abandoned.

BACKGROUND OF THE INVENTION

This invention relates to a process for the preparation of a mixture of methyl- or ethyl-substituted anilines.

Methyl- and ethyl-substituted anilines are useful in a variety of applications such as in the preparation of dyes, herbicides, insecticides, plant growth agents and antiknock agents for gasoline engines. The anilines are generally prepared by nitration of the appropriate methyl benzene followed by reduction of the resulting nitro compound. This process depends upon the availability of the appropriate nitro compound which in some instances is unavailable or available only in limited quantities. For example, m-toluidine is important as an intermediate in dyes and agricultural chemicals. However, in the foregoing nitration-reduction process, only 4% of the toluidines produced are m-toluidine.

European patent application No. 92,103 discloses a process for preparing o-toluidine and/or m-toluidine and/or p-toluidine in two steps: (a) treatment of a toluidine isomer mixture or any undesired toluidine isomer with an isomerization catalyst from the series of the synthetic zeolites of the pentasil type, (b) isolation of the desired or one of the desired isomers from the mixture of isomers formed in step (a) through selective adsorption on a medium or large pore zeolite and subsequent desorption.

U.S. Pat. No. 3,868,420 discloses a process for producing phenylamines alkylated in the ortho and/or para positions by alkyl groups of 1 to 4 carbon atoms and unsubstituted on the amino group which comprises reacting a suitable phenylamine with an alkanol of 1 to 4 carbon atoms in the vapor phase at a temperature of from 350° to 450° C. in the presence of an aluminum oxide catalyst or an aluminum oxide/molybdenum oxide mixed catalyst.

U.S. Pat. No. 3,931,298 discloses a process for converting hydroxy-substituted aromatic compounds to the corresponding amine by reacting the aromatic hydroxy compound with ammonia in the presence of a catalytic amount of a cyclohexane and in contact with a hydrogen-transfer catalyst. U.S. Pat. No. 3,960,962 discloses a similar process wherein the catalyst comprises metallic palladium bonded to a phosphinated polystyrene resin.

U.S. Pat. No. 4,188,341 discloses a process for making 2,6-dimethylaniline or an N-substituted 2,6-dimethylaniline comprising reacting an enamine of a specified formula at a temperature of between −30° C. and 150° C. with acrolein in the presence of an inert aprotic solvent and heating the resulting reaction product to a temperature of between 100° and 400° C. in the presence of a hydrogen-transfer catalyst and an amine of the formula $RNH_2$ wherein R is —H or a specified lower alkyl.

Japanese Kokai No. 53-28128 discloses a process for para-methylation of anilines comprising reacting an aniline having para-hydrogens with methanol in the presence of an alkali metal synthetic zeolite catalyst, particularly NaY zeolite. Preparation of 2,4-dimethylaniline from o-toluene and the preparation of p-toluidine from aniline are specifically disclosed.

Inoue et al., Seikyu Gakkaishi, 15, 372 (1972) studied the methylation of aromatic compounds with methanol in vapor or liquid phase on various catalysts and specifically report the orthomethylation of aniline with methanol using 10% $MgO/Al_2O_3$ catalyst to produce o-toluidine.

Japanese patent publication No. 28129/1978 discloses demethylation of polymethylanilines, which contain at least more than two methyl groups, in the presence of a catalyst composition of the formula $A_aB_bC_cO_d$ wherein A is titanium; B represents more than one kind of element selected from zinc, zirconium and magnesium; C represents more than one kind of element, selected from vanadium, chromium, manganese, tin, iron, cobalt, nickel, copper, molybdenum, tungsten, barium, calcium; O is oxygen; a is 1, b is 0.05 to about 20, and c is 0 to 1.0.

Japanese patent publication No. 1974-[Showa-49], 29,178 discloses a process for the synthesis of toluidines rich in m-toluidine by dealkylation of xylidines having a methyl group in a meta position in the presence of a dealkylation catalyst such as silica-alumina, alumina, silica, silica-magnesia and magnesia. Matsumoto et al., Chemistry Letters, pages 435 to 438 (1978) disclose a process for preparing m-toluidine by hydrocracking 2,3-xylidine over metal oxide-supported nickel catalysts. The authors disclose that the selectivity of m-toluidine is influenced by side reactions, such as isomerization, and that the extent of isomerization can be related to the acidic character of the metal oxide carriers.

SUMMARY OF THE INVENTION

The present invention provides a process for preparing an isomeric mixture of an alkyl-substituted aniline having the formula

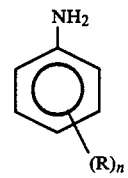

wherein R is a methyl or ethyl group, n is 1 or 2 when R is methyl, and n is 1 when R is ethyl, the process consisting essentially of contacting at least one compound of formula I with a zeolite catalyst at a temperature of from about 250° to 500° C. and at a pressure of from about 10 kPa to 10 MPa, said zeolite catalyst having pores with dimensions of from about 0.5 nm to less than about 0.7 nm and having cages with dimensions no greater than about 0.7 nm, with the proviso that when R is methyl and n=2 the formula I anilines can only be 2,4- 2,5- and 3,4-dimethylanilines.

BRIEF DESCRIPTION OF THE DRAWING

The FIGURE shows the kinetic paths followed by the toluidines to reach equilibrium when isomerization is performed over the zeolite HZSM-5.

DETAILED DESCRIPTION OF THE INVENTION

The isomerization process of this invention is represented by the reaction

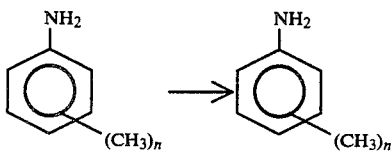

where n equals one or two, and by the reaction

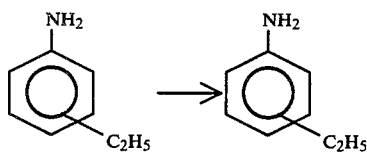

where in each reaction the product is a different isomer than the reactant.

In the process of the invention the total number of methyl or ethyl groups on the primary aniline is substantially conserved. Minor portions of the reactant may undergo reactions in which some of the methyl or ethyl groups are lost. However, under the conditions of this process, the major portion of the reactant undergoes the reaction indicated above in which the number of methyl or ethyl groups on the reactant aniline equals the number on the product aniline.

Zeolite catalysts suitable for use in the process of the invention have pores large enough to accommodate one aromatic molecule but not large enough to allow two aromatic molecules to react with each other. This condition is satisfied by those zeolites with pore aperture dimensions of at least about 0.5 nm but less than about 0.7 nm and having cages with dimensions no greater than about 0.7 nm. As used herein, "pore dimensions" means the aperture dimensions determined from crystal structures analyses, i.e., the crystallographic free diameters of the channels as discussed by Meier et al., "Atlas of Zeolite Structure Types", published by the Structure Commission of the International Zeolite Association, 1978. The free diameter values are based on the atomic coordinates of the type species in the hydrated state and an oxygen radius of 1.35 Å (0.135 nm).

Suitable zeolite catalyst include HZSM-4, HZSM-5, HZSM-8, HZSM-11, HZSM-34, HZSM-35, HZSM-47, H-$\beta$, H-L, NaZSM-5, NaZSM-12, H-mordenite and H-offretite or a mixture of any of the foregoing but HZSM-5 and HZSM-8 are preferred. These zeolite catalysts can be prepared by known procedures. Zeolite HZSM-4 can be prepared according to the method disclosed in U.S. Pat. No. 3,642,434. Zeolite HZSM-5 can be prepared according to the method disclosed in U.S. Pat. No. 3,702,886. Zeolite HZSM-8 can be prepared according to the method disclosed in U.S. Pat. No. 3,766,093. The method disclosed in European patent application publication No. 14,059, particularly Example 7, can be used to prepare zeolite HZSM-11. Zeolites HZSM-34 and HZSM-35 can be prepared by the process disclosed in U.S. Pat. No. 4,086,186 (particularly Example 10) and U.S. Pat. No. 4,016,245 (particularly Example 12), respectively. The method disclosed in U.S. Pat. No. 4,187,283, particularly Example 1, can be used to prepare zeolite HZSM-47. Zeolite H-$\beta$ can be prepared by the procedure disclosed in U.S. Pat. No. 3,308,069. Zeolite NaZSM-5 and zeolite NaZSM-12 can be prepared by the methods disclosed in U.S. Pat. No. 3,702,886 and European Pat. No. 18,089 (particularly Example 2), respectively. Zeolite H-offretite can be prepared by the method disclosed in British Pat. No. 1,188,043. Zeolite H-L and zeolite H-mordenite can be purchased commercially and, as used in the examples, were Linde ELZ-L and Norton Z-900H, respectively. The X-ray diffraction pattern of each zeolite that was prepared for use in the examples was compared with the known X-ray pattern of that zeolite to confirm that the desired zeolite had been prepared.

The toluidine isomerization can be represented as o-toluidine$\rightleftharpoons$m-toluidine$\rightleftharpoons$p-toluidine with no direct interconversion of o- and p-toluidine. For isomerization of the toluidines, depending on the reactor system employed, a solvent may be needed to feed p-toluidine, which is a solid, to the reactor system. A convenient solvent is aniline, however, any other suitable solvent can be used, such as benzene, toluene, xylene and related solvents.

In the process of the invention isomerization of 2,4-, 2,5-, and 3,4-dimethylanilines (DMA) occurs with interconversion between any two of these three isomers; i.e.,

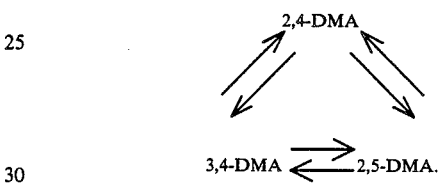

The other three isomers 2,3-, 2,6-, and 3,5-dimethylanilines, are neither formed from 2,4-, 2,5-, or 3,4-dimethylaniline over the herein prescribed catalysts, nor are the 2,3-, 2,6-, and 3,5-dimethylanilines converted by these catalysts.

In the process of the invention at least one substituted aniline of formula I is contacted with a catalytic amount of any of the zeolite catalysts set forth herein. A temperature of from about 250° to 500° C., preferably from about 300° C. to 400° C. is employed. The process is conducted at a pressure of from about 10 kPa to 10 MPa, preferably from about 100 kPa to 1 MPa. Suitable reaction times are from about 0.1 second to 10 hours. The process of the invention can be carried out in either a liquid or gas phase and can be conducted in batch or continuous mode.

The invention is further illustrated by the following examples in which all temperatures are in degrees Celsius and all percentages are by weight unless otherwise stated.

EXAMPLES 1 to 3

Isomerization of toluidines when contacted with zeolite HZSM-5 was demonstrated by passing an approximately 1:1 (mole ratio) toluidine/aniline feed solution over 3 g of zeolite HZSM-5, at atmospheric pressure and various reaction temperatures, feed solution flow rates and nitrogen gas flows in a 13 cm (5 inch) long, 1 cm ($\frac{3}{8}$ inch) diameter Vycor ® reactor heated with a split-tube furnace. After the process had operated for 20 minutes, the product for the next 5 minutes was collected and analyzed using a 6.1 m (20 feet) by 0.32 cm ($\frac{1}{8}$ inch) stainless steel column packed with polyethylene oxide and 1% KOH on 80/100 mesh diatomaceous earth. Elution was carried out isothermally at 200° with a nitrogen gas flow of 40 cc/minute. The retention times increased in the order aniline, ortho-, para-, and meta-toluidine.

Feeding each toluidine/aniline solution to HZSM-5 at increasingly severe reaction conditions (longer contact times and/or higher temperatures) results in the kinetic paths shown in the FIGURE. Except at the very highest temperatures, no more aniline is found in the product than was present in the starting material. Neither di- nor trimethylanilines are formed. The reaction conditions and results are summarized in Table I. The maximum meta distribution which this catalyst produces starting from p-toluidine is 58 mole %. The same equilibrium concentration, 17 mole % p-toluidine, 52 mole % m-toluidine, and 31 mole % o-toluidine, of the three toluidine isomers is obtained no matter which toluidine is used as the feed. There is no direct interconversion of o- and p-toluidine and the reaction may be described essentially in terms of shifts of methyl group to neighboring ring sites. The relative rates of the four reactions needed to describe this system are given in the Figure.

EXAMPLE 4

To demonstrate that aniline is not a necessary reactant in Examples 1–3, Example 3 was repeated using as the feed pure m-toluidine at a rate of 2.2 ml/hr with a N$_2$ gas flow rate of 10 ml/min and with a reaction temperature of 375° and atmospheric pressure. The product was analyzed using a procedure similar to that described for Examples 1–3 and found to contain 54 mole % m-toluidine, 29 mole % o-toluidine, 15 mole % p-toluidine, and 1.7 mole % aniline.

TABLE I

| Example No. | Toluidine in Feed | Feed Flow Rate ml/hr | N$_2$ Gas Flow Rate ml/min | Reaction Temp ° | Product Composition (mole %) | | | |
|---|---|---|---|---|---|---|---|---|
| | | | | | Aniline | o-Toluidine | p-Toluidine | m-Toluidine |
| 1 | p-toluidine | 1.5 | 50 | 357 | 55 | 0.5 | 31 | 13 |
| | | | | 377 | 55 | 1.1 | 24 | 19 |
| | | | | 409 | 54 | 2.1 | 22 | 22 |
| | | | | 416 | 54 | 10 | 9.1 | 25 |
| | | 3.0 | 25 | 390 | 51 | 1.5 | 29 | 18 |
| | | | | 417 | 52 | 4.7 | 18 | 25 |
| | | | | 422 | 52 | 7.6 | 13 | 27 |
| | | | | 445 | 51 | 9.5 | 12 | 27 |
| | | | | 450 | 52 | 12 | 9.2 | 27 |
| | | | | 463 | 51 | 13 | 8.7 | 25 |
| | | | | 495 | 52 | 15 | 8.0 | 24 |
| 2 | o-toluidine | 3.0 | 10 | 365 | 49 | 48 | — | 1.5 |
| | | | | 414 | 49 | 46 | 0.6 | 3.4 |
| | | | | 415 | 50 | 43 | 1.3 | 5.6 |
| | | | | 447 | 50 | 28 | 5.1 | 16 |
| | | | | 470 | 50 | 20 | 7.3 | 21 |
| | | | | 500 | 51 | 16 | 8.0 | 24 |
| 3 | m-toluidine | 3.0 | 10 | 360 | 51 | 0.9 | 2.6 | 45 |
| | | | | 418 | 51 | 6.3 | 8.8 | 33 |
| | | | | 430 | 51 | 7.8 | 9.3 | 32 |
| | | | | 450 | 50 | 13 | 9.1 | 28 |
| | | | | 464 | 52 | 14 | 8.4 | 25 |
| | | | | 496 | 51 | 15 | 8.2 | 25 |

EXAMPLES 5 to 14

The process of the invention was carried out using various suitable zeolite catalysts and using a procedure similar to that set forth in Examples 1–3. A feed solution of approximately 1:1 (mole ratio) p-toluidine/aniline was passed over 3 g of the catalyst at atmospheric pressure and at various reaction temperatures at a feed solution rate of 2.2 ml/hr and a nitrogen gas flow of 10 ml/min. The catalyst, reaction conditions, and results are shown in Table II.

EXAMPLES 15 to 20

Using a procedure similar to that described in Examples 1–3, a feed solution of approximately 1:1 (mole ratio) p-toluidine/aniline was passed over various amounts of different catalysts at atmospheric pressure and various reaction temperatures at a feed rate of 2.2 ml/hr and a nitrogen gas flow of 10 ml/min. The reaction conditions and results are shown in Table III.

EXAMPLES 21 to 23

Isomerization of 2,4-, 2,5-, and 3,4-dimethylanilines in the presence of zeolite HZSM-5 was effected by passing a dimethylaniline over 3 g of zeolite HZSM-5, at atmospheric pressure and various reaction temperatures at flow rate of 3 ml/hr and a nitrogen gas flow rate of 10 ml/min in a vapor phase reactor similar to that described in Examples 1–3. After the process operated for 30 minutes, the product for the next 5 minutes was collected and analyzed by gas chromatography using a procedure similar to that of Examples 1 to 3. Results are summarized in Table IV.

TABLE II

| Example No. | Catalyst | Reaction Temp. ° | Product Composition (mole %) | | | |
|---|---|---|---|---|---|---|
| | | | Aniline | o-Toluidine | p-Toluidine | m-Toluidine |
| 5 | HZSM-5 | 300 | 51 | — | 44 | 5.0 |
| | | 400 | 51 | 15 | 8.3 | 25 |
| 6 | HZSM-5 | 300 | 51 | — | 48 | — |
| | | 400 | 52 | 4.5 | 19 | 24 |
| | | 500 | 53 | 15 | 7.4 | 23 |
| 7 | HZSM-5 | 300 | 52 | — | 47 | 0.6 |
| | | 400 | 51 | 13 | 8.1 | 26 |
| | | 500 | 59 | 13 | 6.3 | 20 |
| 8 | HZSM-8 | 300 | 52 | 0.6 | 47 | 0.6 |
| | | 400 | 53 | 7.4 | 16 | 24 |
| | | 500 | 56 | 14 | 7.1 | 22 |
| 9 | HZSM-11 | 300 | 51 | — | 48 | — |
| | | 400 | 51 | 0.5 | 46 | 1.8 |
| | | 500 | 52 | 12 | 10 | 26 |

TABLE II-continued

| Example No. | Catalyst | Reaction Temp. ° | Product Composition (mole %) | | | |
|---|---|---|---|---|---|---|
| | | | Aniline | o-Toluidine | p-Toluidine | m-Toluidine |
| 10 | NaZSM-5 | 300 | 53 | — | 47 | — |
| | | 400 | 52 | 6.3 | 17 | 24 |
| | | 500 | 58 | 13 | 6.6 | 20 |
| 11 | HZSM-34 | 300 | 53 | — | 47 | — |
| | | 400 | 54 | 0.4 | 40 | 5.9 |
| | | 500 | 60 | 4.1 | 17 | 19 |
| 12 | H—β | 300 | 53 | — | 47 | — |
| | | 400 | 55 | 0.8 | 40 | 4.7 |
| | | 500 | 62 | 7.7 | 8.2 | 20 |
| 13 | H—L | 300 | 51 | — | 49 | — |
| | | 400 | 54 | 0.6 | 43 | 2.1 |
| | | 500 | 61 | 6.2 | 20 | 8.4 |
| 14 | H—mordenite | 375 | 51 | — | 43 | 5.3 |
| | | 500 | 52 | — | 45 | 2.6 |

TABLE III

| Example No. | Catalyst | Quantity of Catalyst-grams | Reaction Temp. ° | Product Composition (mole %) | | | |
|---|---|---|---|---|---|---|---|
| | | | | Aniline | Toluidine | Toluidine | Toluidine |
| 15 | HZSM-4 | 1.5 | 300 | 41 | 0 | 43 | 0.2 |
| | | | 400 | 50 | 0.4 | 44 | 2.1 |
| | | | 500 | 50 | 2.3 | 30 | 14 |
| 16 | HZSM-11 | 3.0 | 400 | 47 | 16 | 11 | 26 |
| 17 | HZSM-35 | 1.3 | 400 | 52 | — | 41 | 1.8 |
| | | | 500 | 58 | 2.8 | 28 | 10 |
| 18 | HZSM-47 | 1.5 | 300 | 51 | 0.6 | 49 | — |
| | | | 400 | 51 | 0.7 | 48 | — |
| | | | 500 | 53 | 0.5 | 43 | 3.2 |
| 19 | NaZSM-12 | 1.4 | 300 | 48 | 0.9 | 48 | — |
| | | | 400 | 42 | 2.2 | 36 | 2.6 |
| | | | 500 | 52 | 3.7 | 26 | 17.1 |
| 20 | H-offretite | 1.7 | 300 | 52 | — | 48 | — |
| | | | 400 | 52 | — | 42 | 2.8 |
| | | | 500 | 60 | 3.2 | 22 | 14 |

TABLE IV

| Ex. No. | DMA | Reaction Temp. (°) | Product Composition (mole %) | | |
|---|---|---|---|---|---|
| | | | 2,4-DMA | 2,5-DMA | 3,4-DMA |
| 21 | 2,4-DMA | 385 | 88 | 7.6 | 4.5 |
| | | 412 | 69 | 22 | 9 |
| | | 435 | 57 | 31 | 11 |
| | | 454 | 52 | 35 | 13 |
| | | 474 | 47 | 38 | 15 |
| | | 501 | 40 | 40 | 20 |
| 22 | 2,5-DMA | 355 | 2.1 | 93 | 4.6 |
| | | 375 | 3 | 89 | 8 |
| | | 420 | 15 | 68 | 17 |
| | | 433 | 26 | 52 | 22 |
| | | 455 | 26 | 51 | 23 |
| | | 502 | 30 | 46 | 24 |
| 23 | 3,4-DMA | 380 | 4 | 14 | 83 |
| | | 420 | 9 | 32 | 59 |
| | | 455 | 12 | 39 | 50 |
| | | 487 | 19 | 43 | 38 |

EXAMPLES 24 and 25

Isomerization of an ethylaniline in the presence of zeolite HZSM-5 was effected using a procedure similar to that described in Examples 1–3. A feed solution of approximately 1:1 (mole ratio) ethylaniline:aniline was passed over 3 g of zeolite HZSM-5 catalyst at a rate of 2.2 ml/hr with a $N_2$ gas flow rate of 10 ml/min. The reaction conditions and results are shown in Table V.

TABLE V

| Ex. No. | Ethylene in Feed | Reaction Temp. (°) | Product Composition (mole %) | | | |
|---|---|---|---|---|---|---|
| | | | Aniline | Ethylaniline | | |
| | | | | o- | p- | m- |
| 24 | o-ethyl-aniline | 295 | 45 | 53 | 0.3 | 1.9 |
| | | 295 | 45 | 52 | 0.3 | 2.1 |
| | | 300 | 47 | 45 | 1.1 | 7.1 |
| | | 300 | 48 | 48 | 0.9 | 5.4 |
| | | 330 | 47 | 32 | 3.5 | 18 |
| | | 360 | 49 | 22 | 4.8 | 24 |
| | | 390 | 58 | 12 | 5.9 | 25 |
| | | 400 | 59 | 11 | 5.9 | 24 |
| 25 | p-ethyl-aniline | 300 | 46 | 1.1 | 38 | 14 |
| | | 300 | 45 | 1.6 | 27 | 27 |
| | | 330 | 47 | 3.1 | 24 | 26 |
| | | 360 | 48 | 3.1 | 13 | 33 |
| | | 390 | 52 | 7.8 | 8.2 | 31 |
| | | 420 | 60 | 8.1 | 6.2 | 25 |

The invention being claimed is:

1. A process for preparing an isomeric mixture of an alkyl-substituted aniline having the formula

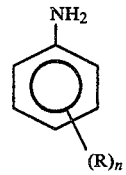

wherein R is a methyl or ethyl group, n is 1 or 2 when R is methyl, and n is 1 when R is ethyl, the process consisting essentially of contacting at least one compound of formula I with a zeolite catalyst at a temperature of from about 250° to 500° C. and at a pressure of from about 10 kPa to 10 MPa, said zeolite catalyst having pores with dimensions of from about 0.5 nm to less than about 0.7 nm and having cages with dimensions no greater than about 0.7 nm, with the proviso that when R is methyl and n=2 the formula I anilines can only be 2,4-, 2,5- and 3,4-dimethylanilines.

2. A process according to claim 1 wherein contacting with the catalyst is performed for a time of from about 0.1 second to 10 hrs.

3. A process according to claim 2 wherein the catalyst is selected from the group consisting of HZSM-4, HZSM-5, HZSM-8, HZSM-11, HZSM-34, HZSM-35, HZSM-47, H-β, H-L, NaZSM-5, NaZSM-12, H- mordenite and H-offretite or a mixture of any of the foregoing.

4. A process according to claim 3 wherein the catalyst is HZSM-5.

5. A process according to claim 3 wherein the catalyst is HZSM-8.

6. A process according to claim 3 wherein the contacting is performed in the presence of a solvent.

7. A process according to claim 6 wherein the solvent is aniline.

8. A process according to claim 3 wherein R is a methyl group.

9. A process according to claim 8 wherein n is 1.

10. A process according to claim 8 wherein n is 2.

11. A process according to claim 8 wherein the product is approximately an equilibrium mixture of isomers.

12. A process according to claim 8 wherein the catalyst is HZSM-5 or HZSM-8.

13. A process according to claim 12 wherein the catalyst is HZSM-5.

14. A process according to claim 12 wherein the catalyst is HZSM-8.

* * * * *